United States Patent [19]

Ries et al.

[11] 4,150,970

[45] Apr. 24, 1979

[54] GROWTH REGULATOR FOR PLANTS

[75] Inventors: Stanley K. Ries, East Lansing; Charles C. Sweeley, Okemos, both of Mich.

[73] Assignee: Board of Trustees of Michigan State University, East Lansing, Mich.

[21] Appl. No.: 756,142

[22] Filed: Jan. 3, 1977

[51] Int. Cl.$^2$ .............................................. A01N 5/00
[52] U.S. Cl. .................................................... 71/122
[58] Field of Search .......................................... 71/122

[56] References Cited

U.S. PATENT DOCUMENTS

| | | | |
|---|---|---|---|
| 3,205,059 | 9/1965 | Roberts | 71/122 |
| 3,556,767 | 1/1971 | Mecklenborg | 71/122 |

OTHER PUBLICATIONS

Crosby et al., Plant Growth Substances (1961), pp. 57–69.

*Primary Examiner*—Catherine L. Mills
*Attorney, Agent, or Firm*—Ian C. McLeod

[57] ABSTRACT

This invention relates to the use of a specific chemical compound, 1-triacontanol ($CH_3(CH_2)_{28}CH_2OH$) as a growth regulator for plants. Triacontanol acts as a growth stimulant on a wide range of plants to increase dry weight gains, water uptake, water use efficiency and protein synthesis in treated plants. Triacontanol can be applied in different ways with equal efficiency, either e.g., as a foliar spray, as a soil drench, as a side dressing or as a part of an insecticide or fertilizer application, etc. Surprisingly, it has been found that triacontanol treated plants grown in the dark increased in leaf area and in dry weight and the treated plants continued synthesizing protein.

20 Claims, 6 Drawing Figures

GROWTH REGULATOR FOR PLANTS

BACKGROUND OF THE INVENTION

Growth regulators for plants have been known for some time. Generally, such regulators have been specific in the plant or type of plant which can be effected. Further, the known regulators generally regulate or increase one growth characteristic, i.e., dry weight increase, water uptake, leaf area increase, etc., at the expense of other growth characteristics.

There have been published reports that aliphatic organic compounds, many of which are known to be natural products, possess growth inhibiting or promoting activities (see the publication of Dieter Gross in *Phytochem.* 14, 2105, 1975). Fatty alcohols with chain links $C_9$, $C_{10}$, and $C_{11}$ are active in inhibiting axillary and terminal bud growth, as reported by Cathey et al in *Science*, 153, 1382 (1966) and by Stephens et al in the *Journal of Agricultural Food Chemistry* at 15, 972 (1967). The Brassins, a group of unidentified compounds, are capable of inducing the elongation of plants and have a glyceride structure, see Mitchell et at in *Nature* 225, (1970). The primary alcohol 1-docosanol, isolated from Maryland Mammoth tobacco (Nicotiana Tobacum L.) was shown to increase growth using the oat first-internode method, as published by Vlitos et at in *Nature* 183, 462 (1959) and Crosby et al in *Plant Growth Substances*, Iowa State University Press, Ames, Iowa, 57 (1961). Other synthetic alcohols with 17–22 carbon atoms and their acidic esters also showed activity. 1-Triacontanol was tested, but was not active with this test.

Prior to the present invention, there was no known natural or synthetic growth regulator capable of effective use on a wide range of crops throughout the world. The present invention provides a growth regulator which is effective under a wide range of conditions and on many different species of crops.

BRIEF DESCRIPTION OF THE PRESENT INVENTION

The present invention proposes the use of a specific chemical compound 1-triacontanol $(CH_3(CH_2)_{28}CH_2OH)$ as a growth regulator capable of utility under widely varying conditions and on a wide variety of crop species. So far as can be presently determined, triacontanol is unique in its properties as a plant regulator since the most closely analogous compounds such as octocosanol $CH_3(CH_2)_{26}CH_2OH$, triacontane $CH_3(CH_2)_{28}CH_3$ and octocosanoic acid $CH_3(CH_2)_{26}COOH$ have all proven ineffective.

1-Triacontanol occurs in nature and can be extracted as a crystalline product from alfalfa.

It has been found that side dressings of alfalfa in wheat, for instance, increases the crop yield, but massive doses of alfalfa are required to obtain the desired yield increase. Triacontanol, when extracted from alfalfa and purified or when utilized as a pure, synthetic material, substantially increases crop growth when utilized in applications as low as 0.4 grams per acre. Such applications are effective on a wide range of plants, e.g., rice, wheat, corn, tomatoes, beans, barley and the like to increase dry weight, growth, water uptake, water use efficiency and protein synthesis in the treated plants. Callus cell cultures of tobacco, tomato, potato, bean and barley also showed significant increases in growth when treated with 1-triacontanol.

OBJECTS

It is an important object of this invention to provide a growth stimulant for plants, capable of wide geographic use, applicable in several ways to a wide variety of plant species, and effective in extremely small amounts.

Another object of this invention is the provision of a growth regulator for a wide variety of crop species and having the capacity to promote growth of the crop and to stimulate dry weight gains and protein synthesis under conditions of darkness.

It is a further object to provide a growth stimulant for plants, such as rice, the stimulant being applicable as a soil drench or as an additive to irrigation water to provide a plant growth environment in which leaf growth, dry weight, water uptake and protein synthesis are all appreciably increased.

DETAILED DESCRIPTION OF THE INVENTION

1-Triacontanol, also known as myricyl alcohol having the formula $CH_3(CH_2)_{28}CH_2OH$, is a long chain aliphatic alcohol having a molecular weight of 438.83, a melting point of 88 degrees C. and a density of 0.777. 1-Triacontanol (hereinafter referred to as triacontanol) is relatively water insoluble, is soluble in alcohol and is very soluble in ether and benzene.

Triacontanol at room temperature is a crystalline material which, for plant application use, may be dissolved in chloroform, benzene, or other organic solvent and then emulsified with water. The solubility limit of triacontanol in water is about 0.3 milligrams per liter. In some cases, this amount is sufficient for use, and the direct solution in water can be used. As will be hereinafter explained, triacontanol is effective in extremely small amounts and consequently the formation of active emulsions containing the requisite amounts of triacontanol is easily accomplished with an organic solvent and an emulsifying agent such as "Tween 20".

As utilized herein, the term "aqueous dispersion" encompasses direct water solutions of triacontanol and aqueous emulsions, slurries and the like of triacontanol with dispersing agents, emulsifiers, etc. The triacontanol, preferably as an extremely dilute aqueous emulsion, can be applied to the plants to be treated in any desired manner. For example, crystalline triacontanol can be added directly to irrigation water or the triacontanol may be greatly diluted with water and utilized as a soil drench. It has been found that the use of aqueous solutions or emulsions as a foliar spray is quite effective, while the material can also be applied as a side dressing in the soil adjacent the roots of the plant. In the laboratory, the triacontanol can be added to the nutrient solution, or it may be placed in proximity to the plant as a paper impregnant. Impregnated paper containing triacontanol can also be utilized as a planting tape or as a side dressing medium. The incorporation of triacontanol as an ingredient of a standard insecticide spray, as from an airplane, may be a feasible manner of application.

Single or multiple applications may be utilized as desired, and the time of application to the plant can be varied substantially, with the application of the triacontanol to seedlings being particularly effective. The use of multiple applications over a period of hours or days may increase the effectiveness of the triacontanol, although it appears that repeated applications are of progressively lesser efficacy. Triacontanol aqueous dispersions can be placed in the soil in conjunction with or adjacent to seed during or after the planting of the seed, or the triacontanol can be readily incorporated into a slow release solid pellet or the like for application into or onto the soil around the seed or plant.

From the foregoing, it is apparent that the triacontanol may be utilized in any desired fashion to provide a growing environment for the plants to be treated. The very limited solubility in water of crystalline triacontanol insures against its loss by moisture leaching in the soil or by washing off in a rain following foliar spray application. The coincidence of solubility at an effective level of treatment (0.3 milligrams per liter) insures proper dosage when added to irrigation water or the like.

The effective amount of triacontanol is extremely minute. For example, it has been found that for corn seedlings, the application of the equivalent of about 0.4 grams per acre is effective and the maximum effectiveness may be obtained at applications on the order of about 4 grams per acre, although as much as about 40 grams per acre can be used. When applied as a soil drench, for example in the treatment of rice seedlings, as little as 0.001 milligram per liter of water is effective with the optimum rate of response being obtained at from about 0.01 to about 0.1 milligrams per liter. The effectiveness of triacontanol at extremely low rates indicates that the tonnage utilized in treatment would be far less than a comparable pesticide, but rather would be similar to pheromones.

In view of the extremely small amounts of triacontanol which are required, it can be readily admixed with water dispersions of insecticide for spray application or even admixed with fertilizer, if such is desired.

One of the outstanding functional characteristics of the triacontanol treatment of plants is its effect in rapidly increasing the water uptake of the plant under treatment. This rapid increase in water uptake indicates that triacontanol may effect transpiration, although perhaps not directly. The increased dry weight accumulations in several species of plants with both foliar and root applications at the extremely low rates (on the order of 0.45 micrograms per rice plant) of triacontanol suggests that the triacontanol may be involved in the growth processes.

At the present time, it is uncertain whether the growth response so strongly indicated by the present data is primarily associated with altered water uptake or with carbon dioxide fixation or with respiration. Mitigating against the transpiration theory of operation of the triacontanol, certain data indicates that the triacontanol treated seedlings took up more total nutrient solution, yet the amount taken up, when expressed in nutrient volume per leaf area, was similar for treated and non-treated plants. Since triacontanol applications significantly increase the leaf area of seedlings within eight hours, it is possible that the expanded leaves account for the effectiveness of the triacontanol. Analysis of the data indicates that the net assimilation in milligrams of plant weight per square centimeter of leaf area per day was appreciably greater, on the order of 37%, for triacontanol treated plants than for the control plants during an initial eight-hour and a subsequent 16-hour period. The relative growth rate (RGR) (increase in milligrams dry weight per milligrams original weight per day) for control in treated plants remained constant. This again indicates that although the triacontanol treated plants increased in weight over the controls, this increase was proportional to the increase in leaf area.

There is a significant difference in the response of triacontanol-treated plants subjected to low light intensities, particularly over relatively short time periods. Triacontanol-treated plants under low light conditions gained as much dry weight and leaf area as the control plants did when subjected to high light conditions. Once again, triacontanol-treated plants took up significantly greater amounts of water per plant but, when water uptake was expressed on a leaf area basis, the triacontanol-treated plants took up more water because of the greater leaf area.

The triacontanol treatment caused rice seedlings to accumulate as much dry weight per unit of leaf area at low light intensities as the control plants did at higher light intensities. The disproportionate leaf area increase is indicated by both the NAR and the LAR during the relatively short growth period. The relative growth rate (RGR) was greater for plants receiving triacontanol than control plants through an eight-hour period.

The effect of triacontanol was even more striking for plants grown in the dark. In the dark, untreated plants decreased in dry weight, as expected. However, triacontanol treated plants gained significantly more weight than the dark controls at both 6- and 24-hour harvests. Further studies indicated that at both 3 and 6 hours, the triacontanol-treated plants contained more dry matter than they did at zero time and more than their dark controls. Although the total plant weight for triacontanol-treated seedlings was not greater after one hour, there was a substantial difference in the dry weight of the unexpanded leaves and leaf sheaths. This data suggests that triacontanol stimulates rice seedlings to fix $CO_2$ which would account for the increase in dry matter accumulation in the dark. A series of confirmatory tests run with and without $CO_2$ in the air clearly shows that triacontanol stimulates plants, such as rice seedlings, to fix $CO_2$ in the dark. It also appears that triacontanol treated plants continue the synthesis of protein in the dark, as well as fixing more $CO_2$. There is a total increase in protein per plant for the triacontanol-treated plants of 30% or more when compared with the dark control and of 18% more than the plant prior to treatment, in tests conducted over a relatively short time.

While the phenomenon of dry weight increases by rice seedlings in the dark by the use of triacontanol is not fully understood, it is believed that triacontanol may alter the permeability of the plant membranes to allow the availability of the substrate, thereby accommodating $CO_2$ fixation and protein synthesis in the dark.

In a specifically directed study, triacontanol was found to increase the growth of "In Vitro" plant cell cultures. Tobacco callus cultures were investigated more thoroughly, although in Vitro cell cultures of tomato, potato, barley and bean also showed significant increases in growth. In view of this effect on plant cell cultures, triacontanol may be quite useful in plant breeding programs where tissue culture is used to increase desirable plant lines. In this instance, triacontanol may find application as a means of increasing the growth rate of tissue cultures and the like.

The following examples are presented to illustrate the efficacy of the invention, the method of utilization of the invention and the conditions under which the invention may be used.

EXAMPLE I

The first cutting of weed-free, field-dried, 'Pioneer 520' alfalfa was collected. The hay was dried, and the dried hay was ground in 0.1 M potassium phosphate buffer separately at pH 4 and 9, (10 g/500 ml) centrifuged and the supernatant emulsions were extracted with 500 ml of chloroform. The chloroform extracts were yellow at pH 4 and yellow green at pH 9. The resulting fractions were all compared to alfalfa meal at rates equivalent to 400 kg/ha by applying them in a band 2.5 cm to the side and 2.5 cm below seed of field corn (Michigan 396). The chloroform extracts were allowed to evaporate before planting the corn in 17.5 cm clay pots containing a Spinks sandy loam soil in growth chambers under a 25° C., 16 hour day and 20° C., 8 hour night. The untreated meal, the total water soluble extract, and the chloroform extract at pH 9 significantly increased the dry weight of the 26 day old plants. There was no significant increase from any of the fractions extracted at pH 4 or from the water insoluble residue made at pH 9. The chloroform extract from the water soluble fraction of 30 g of hay yielded 111 mg of dry matter. Analysis of this by micro Kjeldahl procedures indicated that insufficient nitrogen was present to act as a nutrient.

Gel exclusion chromatography on Sephadex LH-20 was used to further separate the components of the chloroform extract. The column was 85×0.8 cm, the eluent was chloroform containing % ethanol, and the flow rate 3 ml/20 minutes. The fractions obtained were analyzed by gas-liquid chromatography (Beckman GC-65 interfaced with a Digital PDP 8/e PAMILA Computer System, 1.8 M×2 mm ID glass column containing 10% DC-200 on 60/80 Gas Chrom Q operating at 200° with a helium flow rate of 40 cc/min). After the gel exclusion chromatography, crystals were observed in a fraction between the 11th and 13th tube following the void volume. The crystals were further purified by rinsing with hexane, followed by recrystallization from chloroform. These crystals, because of the small quantity, were compared to the crude chloroform extract based on the quantity of extract placed on the column and assuming only one-half of the crystalline substance was recovered.

Three $\mu$l (equivalent to 1 mg/liter of crude extract) of chloroform solutions from the two fractions were placed on filter papers, dried, and placed in nutrient cultures containing 16 day-old rice seedlings. Each test consisted of 4 replicates with 4 seedlings per container. After 24 hours, more water had been taken up by plants growing on both the crude extract and crystals compared to the control. After 9 days the dry weight of the shoots, roots, and water uptake was similar for the two fractions, and both were greater than the controls. The rice seedlings treated with crystals accumulated 56% more dry weight than the control in nine days. The experimental results are set forth in the following table.

TABLE I

| Alfalfa Fractions | Dry weight (mg) | | | (water uptake) (g/plant) |
|---|---|---|---|---|
| | Shoot | Root | Total | |
| Control | 44 | 25 | 69 | 25.3 |
| Crude extract (1.0 mg/l) | 57 | 29 | 86 | 30.0 |
| Crystals ($\mu$0.5 mg/l) | 59 | 30 | 89 | 31.5 |
| L.S.D. at .05 level | 8 | 3 | 11 | 3.1 |
| Initial wt. | 16 | 18 | 34 | |

EXAMPLE II

After the work of Example I has established that the crystals increased growth and water uptake, a sufficient quantity of crystals were prepared by the technique described in Example I, so they could be weighed accurately and a dose-response test was conducted with rice, corn, and barley. Fifteen day old rice seedlings were treated through the solution or by foliar applications. Eight day-old 'Michigan 396' corn seedlings and thirteen day-old 'Larker' barley seedlings grown in a fertile greenhouse potting soil also received foliar applications. Four corn seedlings and 3 barley plants per clay pot were replicated six times. Foliage was sprayed to the drip point with an atomizer. The spray solution consisted of 50 $\mu$l of chloroform with and without the crystals plus 50 mg of Tween-20 in 50 ml of water. The controls did not vary significantly from unsprayed treatements in previous tests with the crude extract. The rice and barley were harvested eight days after treatment and the corn seven days after application.

The results of these tests are set forth in the following table:

TABLE II

| | Rice grown in nutrient solution Application Method | | | | | |
|---|---|---|---|---|---|---|
| | Filter paper | | Foliar spray | | Crops grown in soil and sprayed | |
| Alfalfa crystals (mg/liter) | Water uptake (g/plant) | Dry wt mg plant | Water uptake (g/plant) | Dry wt (mg/ plant) | Barley (mg/shoot) | Corn (mg/shoot) |
| 0.00 | 36.5 | 109 | 35.4 | 110 | 58 | 355 |
| 0.01 | 44.3 | 132 | 38.8 | 118 | 88 | 466 |
| 0.10 | 44.5 | 135 | 40.8 | 123 | 65 | 405 |
| 1.00 | 46.1 | 139 | 43.0 | 132 | 71 | 429 |
| 1.00 | 46.1 | 139 | 43.0 | 132 | 71 | 429 |
| L.S.D. at .05 level | 5.6 | 18 | 4.4 | 15 | 17 | 66 |

From Table II, it will be seen that both the water uptake and dry weight of the rice plants was increased with increasing rates of the crystals applied either to the nutrient solution or to the foliage. The corn and barley grew best when sprayed with 0.01 mg/liter. No toxic abnormal or atypical morphological changes were observed at the rates reported here.

EXAMPLE III

Synthetic triacontanol in aqueous solution was applied to rice (4 replicates) in nutrient cultures and to "Chico III" tomatoes (6 replicates) grown in soil as previously described. The response of both rice and tomatoes to synthetic triacontanol after seven and six days respectively was similar to that of the natural triacontanol with the optimum rate at between 0.01 and 0.1 mg per liter, as summarized in the following table III:

TABLE III

| Triacontanol (mg/liter) | Rice[1] Water uptake (g/plant) | Dry wt (mg/plant) | Tomatoes[2] Dry wt (mg/shoot) |
|---|---|---|---|
| 0.000 | 32.7 | 81 | 190 |
| 0.001 | 37.0 | 103 | 227 |
| 0.010 | 38.8 | 107 | 251 |
| 0.100 | 39.0 | 106 | 245 |
| 1.000 | 33.4 | 91 | 234 |
| L.S.D. at .05 level | 2.4 | 10 | 33 |
| L.S.D. at .01 level | 3.4 | 14 | 44 |

[1]Treatments applied on filter paper, including control and placed in nutrient solution. The solution was changed after 4 days. Seedlings weighed 57 mg at initiation of test.
[2]Tomatoes grown in greenhouse soil and foliage sprayed, including control.

TESTING METHODS AND PROCEDURES FOR EXAMPLES IV–XVIII

Rice seed cv. IR-8, or Starbonnet was surface treated with 0.1 percent mercuric chloride and planted in 77 cc plastic cups containing vermiculite and watered with one-fourth Hoagland's nutrient solution containing 3 mM of nitrogen at pH 5.0. After 10 days, seedlings were transplanted to 220 cc specimen cups wrapped in aluminum foil and containing 180 cc of the same Hoagland's nutrient solution. Four seedlings were suspended in the solution with a sponge rubber disc. The plants were grown under a 8 h night at 25° C. and a 16 h day at 30° C. with 21 and 8 $\mu$watts per cm$^2$ in the blue and red spectra respectively. In the test with varying light intensity the high light intensity was 30 13 and the low intensity was 15 and 8 $\mu$watts per cm$^2$ for the blue and red spectra respectively. The nutrient solution was renewed every 2 or 3 days. After one week the plants were sorted for size and similar sized plants assigned to the same block for the experiment. Prior to the initiation of a test the plants in each cup were assigned treatment numbers by use of a random number table. This procedure resulted in extremely low coefficients of variation of between 2 and 7 percent for these tests. Sixteen hours prior to a test the foil wrapped cups were tared, and filled with one-half Hoaglands solution containing 6 mM nitrogen. Eighteen $\mu$l of chloroform or chloroform containing 1.8 $\mu$g triacontanol were placed on 2 cm$^2$ of Whatman No. 1 filter papers, air dried and placed in the specimen cups. This concentration of 10 $\mu$g triacontanol/liter was used for all tests described in the following Examples except where specifically indicated to the contrary. Immediately prior to the test the cups were all brought up to 180 ml. including a set of cups without plants to measure evaporation.

Water uptake was measured by weighing the cups after removal of the plants and subtracting the tare and the water evaporated. For tests continued for more than one day, the solution used was measured every 3 days and new Hoagland's added and the pH maintained at 5.0 with sulfuric acid.

The plants were disected at harvest into shoots and roots. The expanded leaves were cut at the ligule and the newest leaf at the point it entered the sheath. The surface area of expanded leaves were measured using a Lambda Model LI-3000 planimeter. The plants were dried to constant weight in an oven at 100° C. and the roots, expanded leaves, and sheaths were weighed separately.

In the tests comparing dry weight accumulation in plants grown either in the absence of $CO_2$ or in normal air were grown as previously described except the test was initiated at the end of the 16 hour light period.

Plants were placed in 20×32 cm glass jars fitted with gas inlet and outlet ports. Three jars containing 2 cups each were used for a total of 24 plants for each treatment. The plants were ventilated with air or freed of $CO_2$ by passing it through ascarite and then humidified. The flow rate was approximately 300 ml/minute. Carbon dioxide-free air was also used to purge the appropriate jars during a two minute period required to place the plants in the jars. The N analyses were done by the automated micro-Kjelldahl procedure of Ferrari (1960).

Growth analysis was conducted according to Evans (1972). The Net Assimulation Rate (NAR) is the increase in plant weight per unit of leaf area over time interval where: W=total weight per plant in mg, T=time in days, and L=leaf area in cm$^2$.

$$NAR = \frac{W_2 - W_1}{T_2 - T_1} \times \frac{\text{Log}_e L_2 - \text{Log}_e L_1}{L_2 - L_1} ;$$

The relative growth rate (RGR) is the increase in plant weight per unit of original weight over a time interval and is obtained by:

$$RGR = \frac{\text{Log}_e W_2 - \text{Log}_e W_1}{T_2 - T_1} .$$

The leaf area ratio is the ratio of leaf area to dry weight of leaves over a time interval.

$$\text{Thus: } LAR = \frac{L_1 + L_2}{W_1 + W_2} .$$

Four to 6 replicates were used in each experiment in a randomized complete block design. The data were submitted to analysis of variance. Means were compared by use of the L.S.D. except where there was only one degree of freedom for treatment. In these instances the F value from the analysis of variance was used for comparison of means.

EXAMPLE IV

To determine the effect of triacontanol on growth and water uptake of IR-8 rice seedlings, the seedlings were prepared as above explained. Alternate seedlings were treated with no triacontanol or with a concentration of 10 $\mu$g triacontanol per liter as above set forth. Leaf area, dry weight and water uptake were determined for each plant at 0 time and at 8, 24, 72 and 216 hour intervals. The results are set forth in Table IV:

TABLE IV

| Time after Treatment (hours) | Amount per Plant | | | | | | | |
|---|---|---|---|---|---|---|---|---|
| | Leaf Area (cm$^2$) | | Dry Wt. (mg) | | Water Uptake | | | |
| | | | | | (ml) | | (ml/cm$^2$ leaf area) | |
| | Triacontanol | | | | | | | |
| | 0 | + | 0 | + | 0 | + | 0 | + |
| zero | 7.2 | | 44.8 | | | | | |
| 8 | 7.6 | 8.2* | 50.8 | 53.4 | 1.8 | 2.0 | 0.24 | 0.25 |
| 24 | 7.8 | 9.0* | 52.5 | 58.6 | 3.0 | 3.2 | 0.39 | 0.35 |
| 72 | 12.1 | 13.7 | 70.9 | 81.7* | 16.21 | 18.4 | 1.33 | 1.34 |
| 216 | 20.3 | 22.4 | 174.5 | 204.0** | 55.5 | 65.5** | 2.73 | 2.92 |

*, **, F value significantly different between triacontanol and control for same parameter within rows at 0.05 and 0.01 level respectively.

The results summarized in Table IV demonstrate that triacontanol applications of 10 μg per liter in the nutrient solution significantly increased the leaf area within 8 hours and the dry weight of the entire plant within 3 days (Table 1). Although separate weights were taken of expanded leaves, the remainder of the shoot and roots, the plants parts all increased similarly so only the total dry weight is shown.

In previous work, water uptake differences were measured within a few days of application ostensibly indicating an effect on transpiration. The data in Table IV indicate that although the triacontanol treated seedlings took up more total nutrient solution the amount taken up expressed in ml/cm$^2$ leaf area was similar for treated and non-treated plants.

EXAMPLE V

IR-8 rice seedlings were grown as above explained and were tested at 8 hour, 24 hour, 72 hour, and 216 hour intervals. Control (no treatment) plants are indicated by "0" and triacontanol treated plants are indicated by "+" in Table V. The Net Assimilation Rate (NAR), the Relative Growth Rate (RGR) and the Lead Area Ratio (LAR) was determined for each plant at each interval. The results were as follows:

TABLE V

| Time after Treatment (hours) | Growth Parameter | | | | | |
|---|---|---|---|---|---|---|
| | NAR | | RGR | | LAR | |
| | | | Triacontanol | | | |
| | 0 | + | 0 | + | 0 | + |
| 0-8 | 2.46 | 3.39 | 0.38 | 0.52 | 0.15 | 0.16 |
| 9-24 | 0.33 | 0.90 | 0.05 | 0.14 | 0.15 | 0.15 |
| 25-72 | 0.94 | 1.03 | 0.15 | 0.17 | 0.16 | 0.16 |
| 73-216 | 1.09 | 1.15 | 0.15 | 0.15 | 0.13 | 0.13 |

From Table V, this growth analysis reveals that the NAR (increase in mg plant wt per cm$^2$ lead area per day) was appreciably greater (37%) for triacontanol treated plants than for the control plants during the first 8 hour and subsequent 16 hour period (Table 2). The values for both control and treated plants for the 9-24 hour period were lower, probably because this measurement included only 6 hours of light. After 24 hours, the NAR was not appreciably different for control and treated plants. The RGR values (increase in mg dry weight per mg original weight per day) for control and treated plants and remained constant during the course of the experiment. This indicates that although the triacontanol treated plants increased in weight over the controls, this increase was concommittant with increases in leaf area.

EXAMPLE VI

This Example presents a growth analysis of 'Starbonnet' rice seedlings treated with triacontanol under different light intensities, "Low" and "High" intensities are defined above, and in the Table VI these designations represent the light to which each plant was subjected.

TABLE VI

| Light Intensity | Growth Parameter | Time After Treatment (hours) | | | | | |
|---|---|---|---|---|---|---|---|
| | | 0-4 | | 5-8 | | 9-16 | |
| | | Triacontanol | | | | | |
| | | − | + | − | + | − | + |
| Low | NAR | 2.30 | 3.77 | 2.43 | 4.14 | 3.00 | 2.81 |
| High | NAR | 4.02 | 6.42 | 4.73 | 3.96 | 3.90 | 3.19 |
| Low | RGR | 0.36 | 0.59 | 0.36 | 0.67 | 0.46 | 0.49 |
| High | RGR | 0.56 | 0.89 | 0.66 | 0.57 | 0.56 | 0.50 |
| Low | LAR | 3.72 | 3.76 | 3.54 | 3.90 | 3.65 | 4.20 |
| High | LAR | 3.36 | 3.31 | 3.37 | 3.45 | 3.49 | 3.74 |

Growth analysis of the data from Table VI indicates that triacontanol caused the rice seedlings to accumulate as much dry weight per cm$^2$ of leaf area at low light intensities as the control plants did at the higher light intensity (Table 3). Leaf area increased disproportionately to the dry weight after 8 hours as indicated by both the NAR and LAR during the 9 to 16 hour period. The RGR was greater for plants receiving triacontanol than control plants through 8 hours. There was a similar response under the higher light intensity for both the NAR and RGR except that the increase occurred during the first 4 hours after treatment. The LAR did not differ appreciably between treatments for any time period under the higher light intensity.

EXAMPLE VII

To determine the response of rice seedlings grown in the dark with and without carbon dioxide, 17 day old "IR-8" rice seedlings were grown in the dark for 6 hours. All the parameters of $CO_2$ vs no $CO_2$ and of triacontanol vs no triacontanol were run. The testing procedures were described above.

The results are set forth in Table VII.

TABLE VII

| $CO_2$ Level | Triacontanol | Dry Wt (mg/plant) | | |
|---|---|---|---|---|
| | | Expanded Leaves | Roots | Whole Plant |
| − | − | 22.7 | 23.6 | 63.1 |
| − | + | 22.4 | 23.2 | 62.0 |
| + | − | 21.7 | 22.3 | 60.6 |
| + | + | 26.7 | 25.6 | 71.9 |
| L.S.D. at 0.05 level | | 1.5 | 1.0 | 3.3 |
| L.S.D. at 0.01 level | | 2.1 | 1.4 | 4.6 |
| Zero Time | | 24.4 | 23.3 | 66.2 |
| Coefficient of Variation (%) | | 5.2 | 3.4 | 4.2 |

This test measures the dry weight accumulation of triacontanol treated and untreated seedlings grown in the presence or absence of the normal level of $CO_2$ in air. The leaves, roots and entire plants of triacontanol treated plants grown in the presence of $CO_2$ gained dry weight from zero time and weighed significantly more than the plants grown in the absence of $CO_2$, and more than plants not receiving triacontanol and grown with or without $CO_2$. A second study supported these results. This clearly shows that triacontanol stimulated rice seedlings to fix $CO_2$ in the dark, accounting for the dry weight increase.

EXAMPLE VIII

The total protein (nitrogen) content of 17 day old "IR-8" rice seedlings was determined, where
(1) the seedlings were grown in the dark,
(2) for six hours
(3) with and without triacontanol, and
(4) in the presence of $CO_2$.
The results are set forth in Table VIII.

TABLE VIII

| Triacontanol | Fourth Leaf | Leaves 1,2&3 | Sheaths | Roots | Entire Plant |
|---|---|---|---|---|---|
| | | mg protein/g | | | |
| − | 356** | 313** | 210* | 184** | 239** |
| + | 396 | 342 | 218 | 197 | 261 |
| Zero Time | 341 | 308 | 202 | 182 | 242 |
| Coefficient of Variation (%) | 4.1 | 3.7 | 2.6 | 2.4 | 1.4 |
| | | mg protein/plant | | | |
| − | 1.25** | 5.72** | 3.42** | 4.10** | 14.49** |
| + | 2.47 | 7.01 | 4.26 | 5.05 | 18.80 |
| Zero Time | 1.26 | 6.38 | 3.73 | 4.63 | 16.00 |
| Coefficient of Variation (%) | 25.3 | 4.5 | 6.5 | 4.4 | 5.8 |

*, **, F value for difference between means significantly different at 0.05 and 0.01 level respectively.

Analyses of the total protein present in the different plant parts indicated that the most newly formed leaf (4th) had a higher concentration of total protein (11%) than the control. The increase in dry weight of these leaves accounted for a doubling of the total protein per leaf. There were also increases in protein concentration of the remaining leaves, sheaths and roots. With the exception of the fourth leaf, all plant parts in the dark control lost protein, as expected. The total increase in protein per plant for the triacontanol treated plants was 30 percent more than the dark control and 18 percent more than the zero time. This indicates that triacontanol treated plants continued synthesizing protein in the dark as well as gaining in total weight.

EXAMPLE IX

To determine the effect of triacontanol methods of treatment, differing amounts of triacontanol were applied to field corn by foliar spray and by drenching the soil. The plants were twelve days old at the time of treatment, and the plants were harvested when forty-two days old. The results are presented in Table IX.

TABLE IX

| Treatment | | | |
|---|---|---|---|
| Method of Application | Triacontanol (mg/l) | Dry Weight (mg/shoot) | % increase |
| Foliar Spray | 0.00 | 334 | |
| " | 0.01 | 408 | 22% |
| " | 0.01 | 463 | 39% |
| Soil Drench | 0.00 | 350 | |
| " | 0.01 | 426 | 22% |
| " | 0.10 | 519 | 48% |

0.01 mg/l triacontanol applied by soil drench corresponds to 0.4 grams per acre. 0.10 mg/l corresponds to 4 grams per acre.

EXAMPLE X

Using the materials and procedures set forth above, dry weight and total protein (nitrogen) content of 18-day-old "IR-8" rice seedlings grown in light and dark for 24 hours with or without triacontanol was determined. Table X sets forth the results:

TABLE X

| Treatments | | Plant Part | | | |
|---|---|---|---|---|---|
| Light | Triacontanol | Expanded leaves | Sheaths | Roots | Entire Plant |
| | | Dry Wt (mg/plant) | | | |
| − | − | 19.4 | 12.1 | 18.2 | 49.7 |
| − | + | 22.0 | 12.8 | 20.3 | 55.0 |
| + | − | 24.8 | 15.5 | 21.7 | 62.0 |
| + | + | 30.3 | 18.0 | 24.6 | 72.9 |
| zero time | | 18.4 | 12.9 | 19.4 | 50.8 |
| | | Protein (mg/g) | | | |
| − | − | 402 | 244 | 169 | 278 |
| − | + | 449 | 246 | 164 | 298 |
| + | − | 395 | 245 | 187 | 284 |
| + | + | 394 | 249 | 192 | 290 |
| zero time | | 380 | 252 | 155 | 261 |
| | | Protein (mg/plant) | | | |
| − | − | 7.80 | 2.95 | 3.08 | 13.83 |
| − | + | 9.88 | 3.18 | 3.33 | 16.39 |
| + | − | 9.79 | 3.79 | 4.04 | 17.62 |
| + | + | 11.95 | 4.50 | 4.72 | 21.17 |
| zero time | | 7.02 | 3.25 | 3.00 | 13.27 |

EXAMPLE XI

In this Example, the experiment determined the growth of "IR-8" rice seedlings by comparing a single application of triacontanol with multiple applications of triacontanol. Triacontanol was applied at the beginning of each indicated period. The results are presented in Tabular form in Table XI.

TABLE XI

| Treatment | ml Water uptake per day (Time period) | | | | | Dry wt (mg/seedling) |
|---|---|---|---|---|---|---|
| | 0–2 | 3–5 | 6–7 | 8–9 | 10–12 | |
| Control | 12.4 | 19.7 | 28.5 | 34.3 | 54.0 | 253 |
| Single Appln. | 13.9 | 21.0 | 30.0 | 35.8 | 56.6[a] | 273 |
| Multiple Applns. | 14.2 | 22.6 | 33.5 | 40.2 | 57.0[a] | 286 |
| L.S.D. at 0.05 level | | | | | | 23 |

[a]Two cup were dry at time of harvest in each treatment.

EXAMPLE XII

Tests were run, under the conditions above described, to determine the response of "Michigan 396" field corn and "Larker" barley to single and multiple foliar applications of triacontanol at 10 g/l. Plants were one week old at time of first treatment and 25 days old at time or harvest. Table XII states the test results.

TABLE XII

| Age of Plants at Treatment (Days) | Dry wt (mg/shoot) | |
|---|---|---|
| | Corn | Barley |
| Control | 435 | 187 |
| 7 | 548 | 205 |
| 12 | 522 | 197 |
| 18 | 486 | 193 |
| 7 and 12 | 542 | 206 |
| 12 and 18 | 614 | 214 |
| 7, 12 and 18 | 562 | 210 |
| L.S.D. at 0.05 level | 123 | 16 |

EXAMPLE XII

These tests were run to determine the response of "Heinz 1350" tomato seedlings to applications of triacontanol in nutrient culture, in two different application methods. The results are tabulated in Table XIII.

TABLE XIII

| Treatments | | |
|---|---|---|
| Application Method | Triacontanol (mg/lc) | Dry wt (mg/seedling) |
| Control | 0 | 352 |
| Filter paper | 0.01 | 382 |
| Filter paper | 0.10 | 430 |
| Foliar | 0.01 | 405 |
| Foliar | 0.10 | 407 |
| L.S.D. at 0.05 level | | 43 |
| L.S.D. at 0.01 level | | 60 |

EXAMPLE XIV

Tests were run to study the effect of single and multiple applications of triacontanol on the growth of "Mich. 396 Field Corn" grown at two Fertility Levels in a greenhouse soil. Plants were treated at 14 days after planting and were harvested 37 days after planting. The following results were obtained (Table XIV).

TABLE XIV

| Treatment | | Dry Weight |
|---|---|---|
| Fertility Level | No. | (g/plant) |
| Low | 0 | 1.015 |
| Low | 1 | 1.297 |
| Low | 5 | 1.696 |
| High | 0 | 1.537 |
| High | 1 | 2.032 |
| High | 5 | 1.913 |
| L.S.D. at 0.05 level | | 0.318 |
| L.S.D. at 0.01 level | | 0.437 |

EXAMPLE XV

To study the growth of 25-day-old "Coho" barley seedlings treated with triacontanol solutions applied to the soil in the greenhouse. Treatments were started when seedlings were 13 days old. The results are tabulated in Table XV.

TABLE XV

| Treatments | | |
|---|---|---|
| Nutrients (mg 20-20-20/L) | Triacontanol (mg/L) | Seedling wt (mg/shoot) |
| 0 | 0.00 | 239 |
| 0 | 0.01 | 275 |
| 0 | 0.10 | 270 |
| 100 | 0.00 | 289 |
| 100 | 0.01 | 310 |
| 100 | 0.10 | 316 |
| 1000 | 0.00 | 403 |
| 1000 | 0.01 | 438 |
| 1000 | 0.10 | 442 |
| L.S.D. at 0.05 level | | 31 |
| L.S.D. at 0.01 level | | 42 |

EXAMPLE XVI

Fourteen day old "Starbonnet" rice seedlings were prepared and treated with triacontanol as explained in Example IV above.

Figure 1:
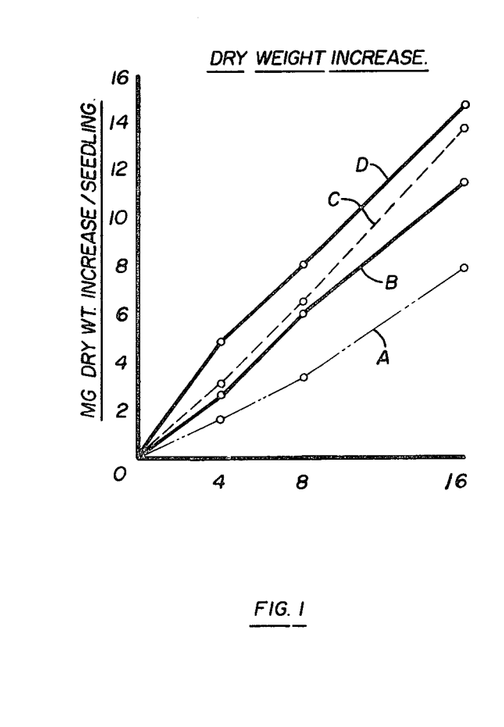
FIGS. 1–3, 4, 5 and 6 are graphic representations of the data of Examples XVI, XVII, XVIII and XIX, respectively.
Figure 2:
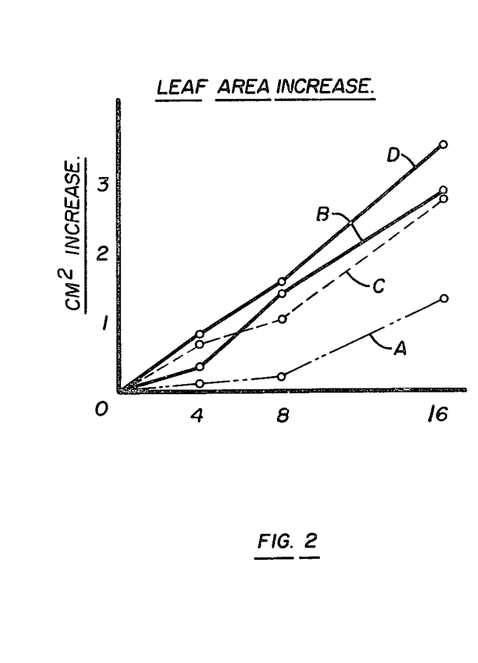
Figure 3:
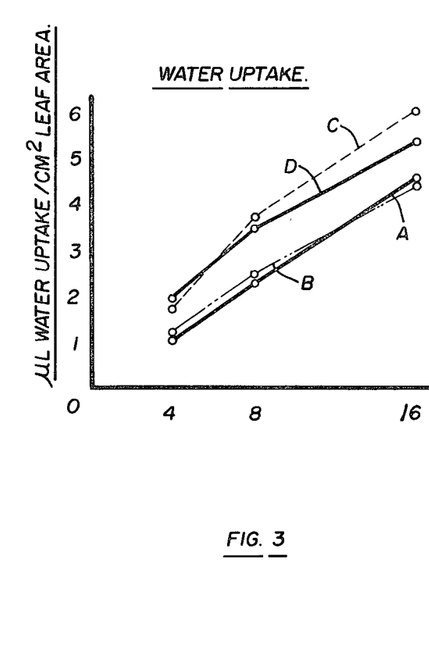

The increase in dry weight and leaf area and the water uptake of the rice seedlings treated with triacontanol under two different light intensities was determined. High light was 30 and 13 $\mu$watts/cm$^2$ and low light 15 and 8 $\mu$watts/cm$^2$ in the blue and red spectra respectively. The plants were exposed to these light conditions 36 hours prior to treatment. At zero time the plants under low light intensity weighed 26.0 mg with 4.41 cm$^2$ leaf area. The high light plants weighed 29.5 mg per plant with 4.01 cm$^2$ leaf area per plant. FIGS. 1, 2 and 3 of the accompanying drawings show the results of these tests. In each Figure, A=low light control; B=low light+triacontanol; C=high light control; and D=high light+triacontanol. Presented in tabular form, the data for FIGS. 1, 2 and 3 appears in Table XVI, as follows:

TABLE XVI

| Treatment | | Percent Increase from Zero Time | | | | | | | | |
|---|---|---|---|---|---|---|---|---|---|---|
| | | Dry Wt. (mg/plant) | | | Leaf Area (cm$^2$) | | | Water Uptake ($\mu$l/cm$^2$ leaf area) | | |
| Light Intensity | Triacontanol (0.01 mg/h) | Time (hr) | | | | | | | | |
| | | 4 | 8 | 16 | 4 | 8 | 16 | 4 | 8 | 16 |
| Low | − | 6 | 13 | 31 | 1 | 2 | 30 | 120 | 257 | 459 |
| | + | 10** | 23** | 45** | 7 | 31** | 64** | 117 | 239 | 453 |
| High | − | 10 | 23 | 48 | 16 | 24 | 65 | 178 | 381 | 603 |
| | + | 16* | 27* | 51** | 19 | 38** | 88** | 192 | 351 | 649 |

*, ** Indicate F values for significant differences between treatments at 0.05 and 0.01 levels respectively.

EXAMPLE XVII

Figure 4:
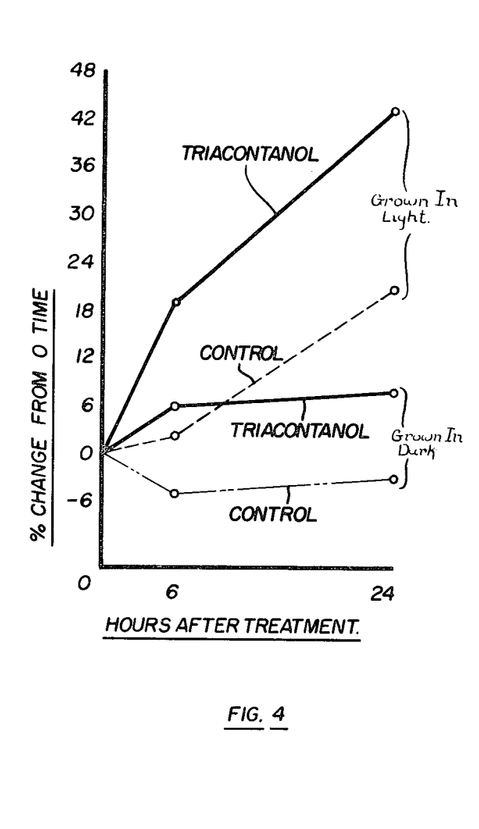

This example was run to determine the percent change in dry weight of whole 18-day-old "IR-8" rice seedlings treated with triacontanol in the light and dark over a 24 hour period expressed as percent change from zero time. The dry weight at zero time was 50.8 mg per seedling. The test results are shown in FIG. 4. In tabular form, the data of FIG. 4 is as follows:

TABLE XVII

| Treatments | | Plant Part | | | |
|---|---|---|---|---|---|
| Light | Triacontanol | Expanded leaves | Sheaths | Roots | Entire plant |
| | | Dry wt (mg/plant) | | | |
| − | − | 19.4 | 12.1 | 18.2 | 49.7 |
| − | + | 22.0 | 12.8 | 20.3 | 55.0 |
| + | − | 24.8 | 15.5 | 21.7 | 62.0 |
| + | + | 30.3 | 18.0 | 24.6 | 72.9 |
| zero time | | 18.4 | 12.9 | 19.4 | 50.8 |
| | | Protein (mg/g) | | | |
| − | − | 402 | 244 | 169 | 278 |
| − | + | 449 | 246 | 164 | 298 |
| + | − | 395 | 245 | 187 | 284 |
| + | + | 394 | 249 | 192 | 290 |
| zero time | | 380 | 252 | 155 | 261 |
| | | Protein (mg/plant) | | | |
| − | − | 7.80 | 2.95 | 3.08 | 13.83 |
| − | + | 9.88 | 3.18 | 3.33 | 16.39 |
| + | − | 9.79 | 3.79 | 4.04 | 17.62 |
| + | + | 11.95 | 4.50 | 4.72 | 21.17 |

TABLE XVII-continued

| Treatments | | Plant Part | | | |
|---|---|---|---|---|---|
| Light | Triacontanol | Expanded leaves | Sheaths | Roots | Entire plant |
| zero time | | 7.02 | 3.25 | 3.00 | 13.27 |

EXAMPLE XVIII

Figure 5:
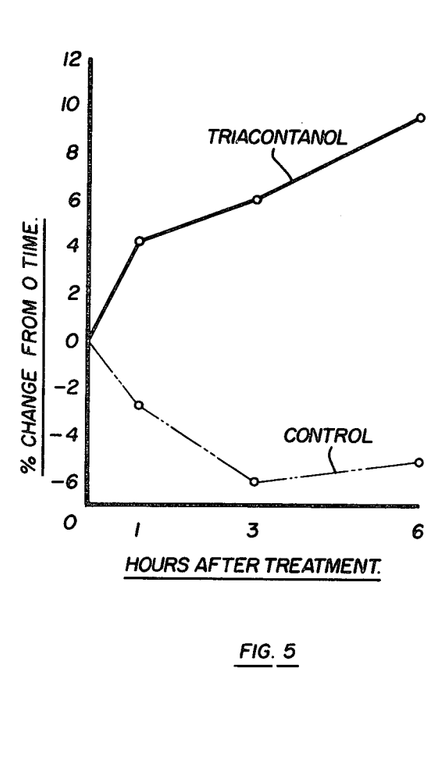

This example was run to determine the percent change in dry weight of whole 15-day-old "IR-8" rice seedlings treated with triacontanol in the dark as compared with a control. The dry weight at zero time was 37.3 mg per seedling. FIG. 5 graphically shows the test results. Expressed in tabular form, the results were:

TABLE XVIII

| Triacontanol (mg/l) | Dry Weight (percent change) Time (hours) | | |
|---|---|---|---|
| | 1 | 3 | 6 |
| 0 | −3 | −6 | −5 |
| 0.01 | 4 | 6* | 10* |

*F value for difference between treatments significant at 0.05 level.

EXAMPLE XIX

Materials:
Cell cultures were separately grown in disposable petri dishes.
The cultures were:
1. Haploid tobacco (*Nicotiana tabacum*, var. Wisconsin 38)
2. Tomato (*Lycopersicon esculentum*, var. marglobe)
3. Potato (*Solanum tuberosum*, var. adveria)
4. Bean (*Phaseolus vulgaris*, var. seafarer)
5. Barley (interspecific cross of *Hordeum vulgare* and *Hordeum jubatum*)

The cultures were grown on the basic medium of mineral salts described by Linsmaier and Skoog (Physiol. Plant, 18,000 (1965)). Vitamins and hormones varied for each tissue (Table X-1) to maintain the tissues in an undifferentiated state. For all of the tissues inositol was 100 mg/liter and agar 1%. Sucrose was 3% for all but the bean which was 2%.

Callus was produced from pith for tobacco, potato and tomato. Bean callus was produced from hypocotyl sections and barley callus from immature ovarian tissue. Subcultures were maintained on the appropriate media.

TABLE XIX-1

Culture mediums. Additions to the mineral salts described by Linsmaier and Skoog.

| Tissue | Thiamine | Pyridoxine | Nicotinic | 2,4-D | IAA | Kinetin |
|---|---|---|---|---|---|---|
| | | | (mg/liter) | | | |
| Tobacco | 1 | — | — | — | 3 | .3 |
| Tomato | 1 | .5 | .5 | 2 | 2 | .3 |
| Potato | 1 | .5 | .5 | .5 | 5 | .3 |
| Bean | 10 | 1 | 1 | 2 | — | — |
| Barley | 1 | .5 | .5 | .5 | 5 | .3 |

Procedures:
Stock solutions of triacontanol were prepared at a concentration of 100 μg/ml. The solvent used was glass distilled benzene. The lower concentrations were obtained by serial dilutions. Treatments were applied to 4.5 cm Whatman #1 filter paper disks in 100 μl aliquots. Controls received 100 μl of glass distilled benzene. The solvent was evaporated for approximately 15 minutes and the filter papers were then placed on the agar medium.

Callus tissue was then broken into pieces of approximately the same size (10 mg) and placed in the petri dishes on the treated filter paper (one piece per dish). For experiments conducted in the light the intensity was approximately 2.0 microwatts/cm$^2$-namometer. Fresh weight measurements were made after 12 days of growth.

The results are set forth in Table XIX-2:

TABLE XIX-2

| Treatment | Tomato | Potato | Barley | Bean |
|---|---|---|---|---|
| Control | 12.0 | 19.5 | 21.0 | 13.0 |
| 10.0 g triacontanol | 16.8 | 23.5 | 35.0 | 19.8 |
| | % of control | | | |
| | 140 | 121 | 167 | 149 |

A stock solution of octocosanol (CH$_3$(CH$_2$)$_{26}$CH$_2$OH) was prepared in the same manner as the triacontanol solutions above described.

Figure 6:
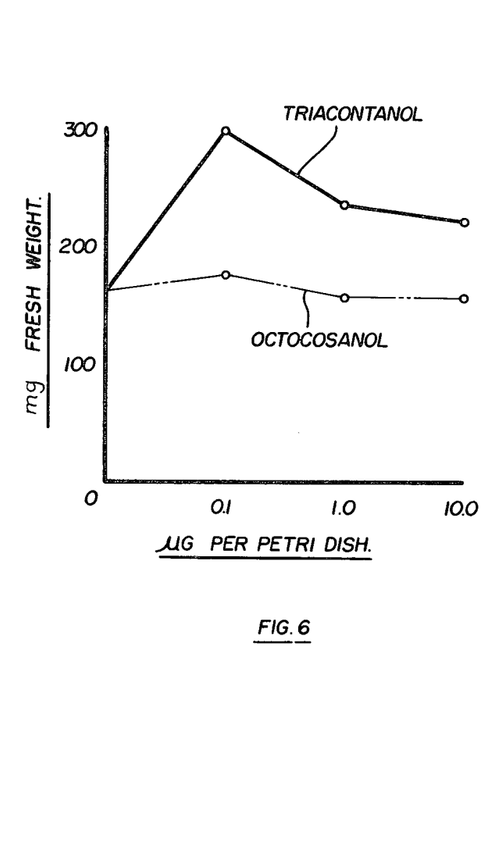

The effect of four concentrations of triacontanol and octocosanol on tobacco callus was determined, using the materials and procedures above described in this Example. The dishes were tared and weighed at the end of 10 days. The results are illustrated in FIG. 6 of the drawings.

The triacontanol treated cultures showed significant increases in growth over the control with an optimum concentration of 0.1 μg per dish. Octocosanol showed no effect on growth.

What we claim is:
1. A method of stimulating plant growth by applying thereto an effective amount of 1-triacontanol.
2. A method of stimulating plant growth by applying thereto an effective amount of pure 1-triacontanol having a melting point of 88° C. and a specific gravity of 0.777 at 95° C.
3. A method for stimulating the growth of crop plants by applying thereto an effective amount of 1-triacontanol.
4. The method of claim 3 wherein the application is to seeds for the crop plants.
5. The method of claim 3 wherein the application is to the roots of the crop plants.
6. The method of claim 3 wherein the application is to leaves of the crop plants.
7. A method as defined in claim 3, wherein the 1-triacontanol is applied at a rate of from about 0.4 grams per acre to about 40 grams per acre of the crop plants.
8. A method as defined in claim 3, wherein the 1-triacontanol is applied in the form of an aqueous dispersion as a spray onto leaves of the crop plants.
9. A method as defined in claim 3, wherein the 1-triacontanol is applied in the form of an aqueous dispersion of 1-triacontanol as a soil drench.
10. A method as defined in claim 3, wherein the 1-triacontanol is applied in the form of an aqueous dispersion as a side dressing around the crop plants.
11. The method as defined in claim 3, wherein an aqueous dispersion is formed by adding 1-triacontanol to irrigation water, and the application is by utilization of the water for irrigating the crop plants.
12. A method as defined in claim 3, wherein the 1-triacontanol is in an aqueous dispersion, wherein the amount of 1-triacontanol in said dispersion ranges from about 0.01 to about 0.1 milligram per liter, and wherein the dispersion is applied either directly to the plants or to soil surrounding the plants.

13. A method of stimulating the growth of a plant comprising the steps of applying an effective amount of an aqueous dispersion containing a plant growth stimulant consisting essentially of at least about 0.001 milligram of 1-triacontanol per liter of water to the plant.

14. A method of stimulating the growth of plant tissue in a growth medium by treating the plant tissue or the plant tissue growth medium with an effective amount of 1-triacontanol and growing the tissue so as to produce an increase in growth of the tissue in comparison to growing the tissue without 1-triacontanol.

15. A method of stimulating the growth of crop plants by spraying the crop plants with an effective amount of an aqueous dispersion of pure synthetic 1-triacontanol.

16. A method as defined in claim 15, wherein the spray is applied at a rate to deliver at least about 0.4 grams of 1-triacontanol per acre of the crop plants.

17. A method as defined in claim 15, wherein the spray is applied at a rate to deliver from about 4 grams to about 40 grams of 1-triacontanol per acre of the crop plants.

18. A method as defined in claim 15 wherein the aqueous dispersion contains between about 0.01 and 0.1 milligram per liter of 1-triacontanol which is sprayed on the crop plants to provide up to about 40 grams of 1-triacontanol per acre.

19. A method of stimulating the growth of a plant selected from rice, wheat, corn, tomatoes or barley by applying thereto an effective amount of 1-triacontanol.

20. A method of stimulating plant growth by applying into or unto soil for the plant an effective amount of 1-triacontanol incorporated in a solid pellet.

* * * * *

UNITED STATES PATENT AND TRADEMARK OFFICE
CERTIFICATE OF CORRECTION

PATENT NO. : 4,150,970
DATED : 1979 April 24
INVENTOR(S) : Stanley K. Ries and Charles C. Sweeley It is certified that error appears in the above-identified patent and that said Letters Patent are hereby corrected as shown below:

Column 1, line 23, "et at" should be --et al--.

Column 1, line 27, "et at" should be --et al--.

Column 5, line 34, "%" should be --1%--.

Column 6, line 24, "has" should be --had--.

Column 6, line 39, "treatements" should be --treatments--.

Column 6, Table II, delete line 5 of table (to remove duplication).

Column 6, Table II, in the third column heading "mg plant)" should be --(mg/plant)--.

Column 7, line 42, "30 13" should be --30 and 13--.

Column 9, line 39, "lead" should be --leaf--.

UNITED STATES PATENT AND TRADEMARK OFFICE
CERTIFICATE OF CORRECTION

PATENT NO. : 4,150,970
DATED : 1979 April 24
INVENTOR(S) : Stanley K. Ries and Charles C. Sweeley It is certified that error appears in the above-identified patent and that said Letters Patent are hereby corrected as shown below:

Column 9, line 54, "lead" should be --leaf--.

Column 11, Table IX, second column, third line, "0.01" should be --0.10--.

Column 12, line 56, "or" should be --of--.

Column 13, line 1, "EXAMPLE XII" should be --EXAMPLE XIII--.

Signed and Sealed this

Sixteenth Day of October 1979

[SEAL]

Attest:

RUTH C. MASON
Attesting Officer

LUTRELLE F. PARKER
Acting Commissioner of Patents and Trademarks